United States Patent [19]

Corvi-Mora

[11] 4,278,796

[45] * Jul. 14, 1981

[54] PIPERAZINES

[76] Inventor: Camillo Corvi-Mora, Via Borgonuovo 9, Milano, Italy

[ * ] Notice: The portion of the term of this patent subsequent to Oct. 31, 1995, has been disclaimed.

[21] Appl. No.: 98,091

[22] Filed: Nov. 28, 1979

Related U.S. Application Data

[63] Continuation of Ser. No. 939,106, Sep. 1, 1978, abandoned, which is a continuation-in-part of Ser. No. 758,725, Jan. 12, 1977, Pat. No. 4,123,530.

[30] Foreign Application Priority Data

Jan. 23, 1976 [IT] Italy .................................. 19517 A/76

[51] Int. Cl.³ .................. C07D 295/14; A01K 31/495
[52] U.S. Cl. ................................................... 544/400
[58] Field of Search ........................................... 544/400

[56] References Cited

U.S. PATENT DOCUMENTS 4,123,530  10/1978  Corvi-Mora .......................... 544/400

*Primary Examiner*—Anton H. Sutto
*Attorney, Agent, or Firm*—Ladas & Parry

[57] ABSTRACT

New piperazine derivatives and homologs thereof of formula $$\begin{array}{c} X \\ \diagdown \\ CH-CH_2 \\ R-N \diagup \diagdown N-(CH_2)_m-CONHR_1 \\ \diagdown \diagup \\ (CH_2)_n \end{array}$$

wherein
  n is equal to 2 or 3 and m to 1, 2 or 3;
  X represents hydrogen or a methyl group;
  R represents hydrogen or a $C_1$ to $C_6$ lower alkyl group or a $C_1$ to $C_3$ hydroxyalkyl group; and
  $R_1$ is a cyclohexyl group of formula $$\begin{array}{c} R_2 \\ \diagup \\ \bigcirc \\ \diagdown \\ R_2 \end{array}$$

wherein $R_2$ is hydrogen or a $C_1$ to $C_6$ lower alkyl group.

The compounds have antiulcer and antisecretory activity.

7 Claims, No Drawings

PIPERAZINES

This application is a continuation of application Ser. No. 939,106 filed Sept. 1, 1978, now abandoned, which is in turn a continuation-in-part of my application Ser. No. 758,725 filed Jan. 12, 1977 which issued as U.S. Pat. No. 4,123,530 on Oct. 31, 1978.

The present invention concerns new piperazine derivatives and homologs thereof of formula

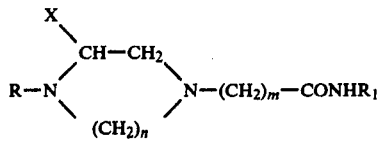

wherein n is equal to 2 or 3 and m to 1, 2 or 3;

X represents hydrogen or a methyl group;

R represents hydrogen or a $C_1$ to $C_6$ lower alkyl group or a $C_1$ to $C_3$ hydroxyalkyl group; and $R_1$ is a cyclohexyl group of formula

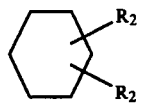

wherein $R_2$ is hydrogen or a $C_1$ to $C_6$ lower alkyl group.

These compounds possess anti-ulcer and anti-secretion properties and are entirely free from anticholinergic activity.

These compounds can be prepared by first reacting an amine of formula $R_1$—$NH_2$ with an acyl chloride derivative (e.g. chloracetyl chloride, chloropropionyl chloride or chlorobutyryl chloride) and, thereafter, condensing the obtained product with piperazine or its derivatives. For instance, the following reaction can be performed:

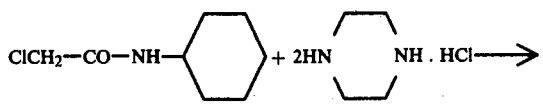

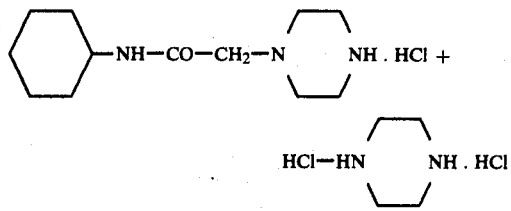

In such instance, one mole of N-(2-chloracetyl)-cyclohexylamine can be reacted with two moles of piperazine and two moles of HCl in water solution.

The reaction works also when 1 mole of piperazine dihydrochloride is used.

It is also possible to use an excess of piperazine in water in ratios of 1:3 to 1:4, however in such case the process is more expensive. On the other hand, the condensation can be carried out in organic solvents, e.g. chloroform or benzene.

The new compounds are also active in the form of their salts with organic or mineral acids, such as, for instance, hydrochlorides, sulfates, phosphates, maleates, succinates and tartrates.

The following is a typical example for preparing the new compounds of the present invention:

Anhydrous piperazine (178.28 g; 2 moles) was dissolved in 1000 ml distilled water. Then HCl 37% (166.6 ml) was added dropwise to provide 2 moles of piperazine mono-hydrochloride. Then N-(chloracetyl)-cyclohexylamine (175.66 g) was added to the above solution of the hydrochloride. The temperature rose to 100° C. and the reaction was completed by refluxing for two hours.

After cooling, the reaction mixture was made alkaline with a 35% NaOH solution and thereafter extracted with chloroform.

The chloroform extract was washed with water, dried with anhydrous $Na_2SO_4$, filtered and evaporated.

The residue was washed with petroleum ether, drained and dried.

The obtained 1-piperazinyl-4-methylene carbonylcyclohexylamine (or N-[1-piperazinylacetyl]-cyclohexylamine), code C/63, was distilled under reduced pressure (b.p. 190° C./0.5 mm); m.p. 111°–112°; yield 65% of theory.

The following compounds have been prepared in the same or analogous manner:

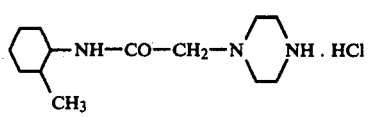

(C/100) m.p. (HCl) 223–224° C.
(base) 102–103° C.

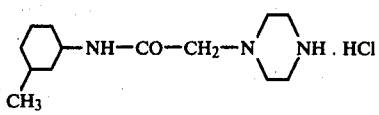

(C/101) m.p. (HCl) 210° C.
(base) 114–115° C.

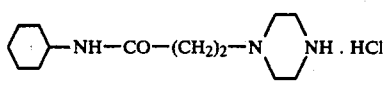

(C/94) m.p. (HCl) 117–178° C.
(base) 95–96° C.

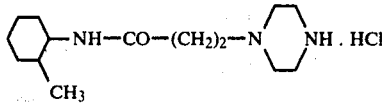

(C/105) m.p. (HCl) 182–183° C.
(base) 110–112° C.

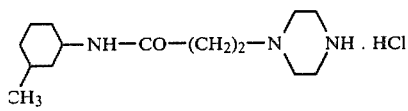

(C/104) m.p. (HCl) 198–199° C.
(base) 77–78° C.

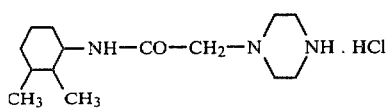

(C/99) m.p. (HCl) 238–239° C.
(base) 62–63° C.

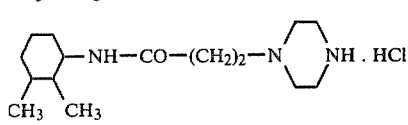

(C/103) m.p. (HCl) 193–194° C.
(base) 133–134° C.

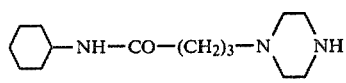

(C/85) m.p. (base) 85° C.

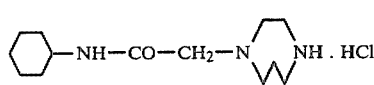

(C/92) m.p. (HCl) 163–164° C.
(base) 20–23° C.

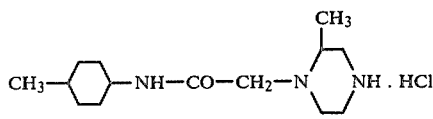

(C/114) m.p. (HCl) 212–213° C.
(base) 96–97° C.

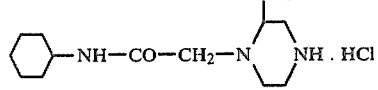

(C/110) m.p. (HCl) 214° C.
(base) 113–114° C.

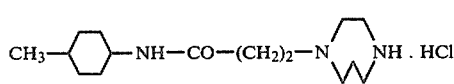

(C/112) m.p. (HCl) 111–112° C.

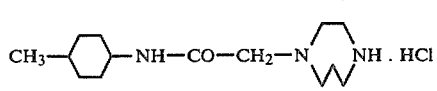

(C/107) m.p. (HCl) 203–204° C.
(base) 60–61° C.

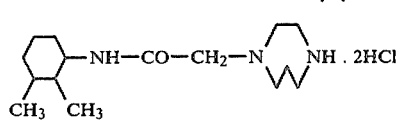

(C/119) m.p. (2HCl) 225° C.

The following table contains the results of pharmacological tests with these compounds. The abbreviations used are iv=intravenous, id=intraduodenal, po=per os, antisecr. act.=antisecretory activity, antiulc. act.=antiulcer activity, PhB/H=phenylbutazon/histamin, all amounts being in mg/kg.

| Compound No. | DL$_{50}$, mice, iv | DE$_{50}$, rats, id antisecr. act. | DE$_{50}$, rats, po antiulc. act. —PhB/H |
|---|---|---|---|
| 100 | 185 | 156 | 150 |
| 101 | 175 | 166 | 200 |
| 94 | 190 | >200 | 150 |
| 105 | 212 | ~200 | 200 |
| 104 | 155 |  | 150 |
| 99 | 203 | 135 | 200 |
| 103 | 217 | 163 | 150 |
| 85 | 140 | 175 | 150 |
| 92 | 118 | 200 | 200 |
| 114 | 145 | ~150 | 75 |
| 110 | 245 | >200 | 100 |
| 112 | 130 | >200 | 50 |
| 107 | 165 | 163 | 100 |
| 119 | 145 | 150 | 70 |

The tests have been made according to the following known methods:

Activity on the gastric secretion (according to Shay, Gastroenterology 5, 43 (1945)).
Phenylbutazone-histamine ulcer (according to Carminati Coll., Boll. Chim. Pharm. 112, 45 (1973)).

The present invention also concerns pharmaceutical compositions which may contain, according to the invention, the new compounds in admixtures with solid or liquid pharmaceutical diluents or carriers and, as desired, in admixtures with other active ingredients or binders.

As examples of pharmaceutical packages, one can mention 50 or 100 mg capsules and ampoules of one of the above compounds. The daily dose will be 1 to 2 ampoules or 2 to 4 capsules.

I claim:

1. A piperazine derivative selected from the group consisting of compounds of the formulae

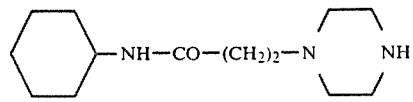

-continued

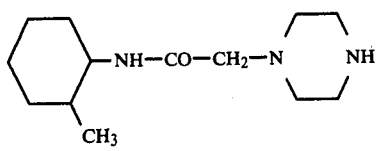

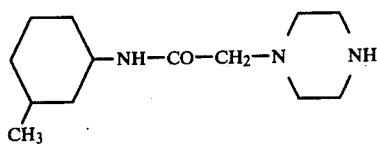

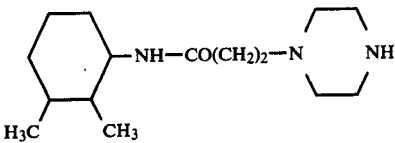

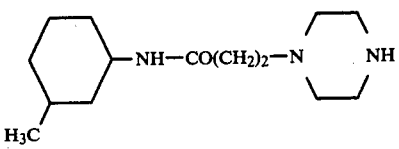

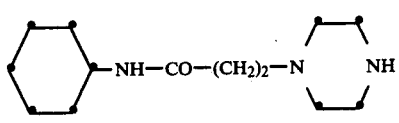

and the pharmaceutically acceptable salts thereof with acids.

2. The compound of formula

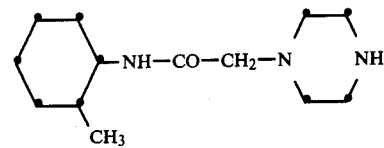

and its pharmaceutically acceptable salts with acids.

3. The compound of formula

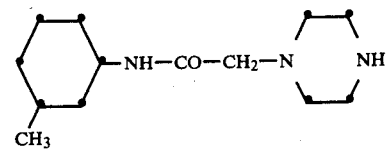

and its pharmaceutically acceptable salts with acids.

4. The compound of formula

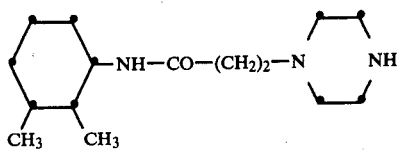

and its pharmaceutically acceptable salts with acids.

5. The compound of formula

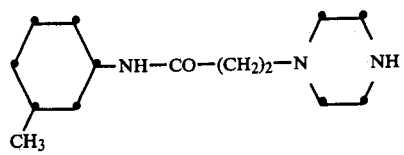

and its pharmaceutically acceptable salts with acids.

6. The compound of formula

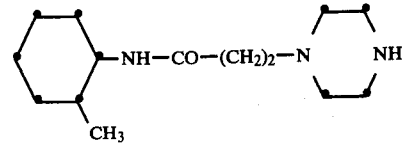

and its pharmaceutically acceptable salts with acids.

7. The compound of formula and its pharmaceutically acceptable salts with acids.

* * * * *